US00PP37805P2

(12) United States Plant Patent
Doll

(10) Patent No.: US PP37,805 P2
(45) Date of Patent: Oct. 20, 2026

(54) ***HYDRANGEA* PLANT NAMED '22B30'**

(50) Latin Name: *Hydrangea scandens*
Varietal Denomination: 22B30

(71) Applicant: Marie-France Doll, La Forêt Fouesnant (FR)

(72) Inventor: Marie-France Doll, La Forêt Fouesnant (FR)

( * ) Notice: Subject to any disclaimer, the term of this patent is extended or adjusted under 35 U.S.C. 154(b) by 0 days.

(21) Appl. No.: 19/629,293

(22) Filed: Mar. 26, 2026

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea scandens* plant named '22B30' that is characterized by its very floriferous blooming habit, its inflorescences with sterile sepals that are bright pink in color, and its broadly upright, mounded, and low growing growth habit.

3 Drawing Sheets

Botanical classification: *Hydrangea scandens*.
Varietal denomination: '22B30'.

CROSS REFERENCE TO A RELATED APPLICATION

This application is related to a European plant breeders' rights application filed on Feb. 19, 2025, application No. 2025/0347. The information for the plant breeders' rights application was received directly from the Inventor.

BACKGROUND OF THE INVENTION

The present invention relates to a new and distinct cultivar of *Hydrangea scandens* and will be referred to hereafter by its cultivar name, '22B30'. '22B30' represents a new lace-cap type *Hydrangea*, a perennial shrub grown for use as a landscape plant.

'22B30' was derived from an ongoing breeding program conducted by the Inventor in in La Forêt Fouesnant, France. The goal of the breeding program is to develop new cultivars of *Hydrangea scandens* with floriferous blooming habits.

The new cultivar originated as a seedling that arose from a cross between unnamed and unpatented plants of *Hydrangea scandens* in 2017. '22B30' was selected as a single unique plant in 2019 from the resulting seedlings.

Asexual propagation of the new cultivar was first accomplished by softwood stem cuttings by the Inventor in La Forêt Fouesnant, France in 2019. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '22B30' as a unique cultivar of *Hydrangea*.

1. '22B30' exhibits a very floriferous habit.
2. '22B30' exhibits inflorescences with sterile sepals that are bright pink in color.
3. '22B30' exhibits a broadly upright, mounded, and low growing growth habit.

Both of the parent plants of '22B30' differ from '22B30' in having less floriferous blooming habits. '22B30' can be most closely compared to the *Hydrangea* cultivars 'French Bolero' (U.S. Plant Pat. No. 32,055) and 'USHYD0405' (U.S. Plant Pat. No. 31,120). 'French Bolero' is similar to '22B30' in having pink flowers, lace-cap inflorescences, and a floriferous blooming habit. 'French Bolero' differs from '22B30' in having inflorescences with sterile sepals that are larger and lighter pink in color, leaves that are more ovate in shape, and a less mounding and less tidy plant habit. 'USHYD0405' is similar to '22B30' in having lace-cap inflorescences. 'USHYD0405' differs from '22B30' in having inflorescences with white sterile sepals and in producing long runners.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Denolf, Facebook, Thompson & Morgan, Telegraph Garden Shop, Coolplants, Houzz, Visions, Plantipp, Dobies, Instagram, Promessedefleurs, Platesdehaies, and PCSDL.

BRIEF DESCRIPTION OF THE DRAWINGS

The accompanying color photographs illustrate the overall appearance and distinct characteristics of the new

*Hydrangea*. The photographs were taken of a 3-year-old plant of '22B30' as grown in 23-cm containers in Waddinxveen, the Netherlands.

Figure 1:
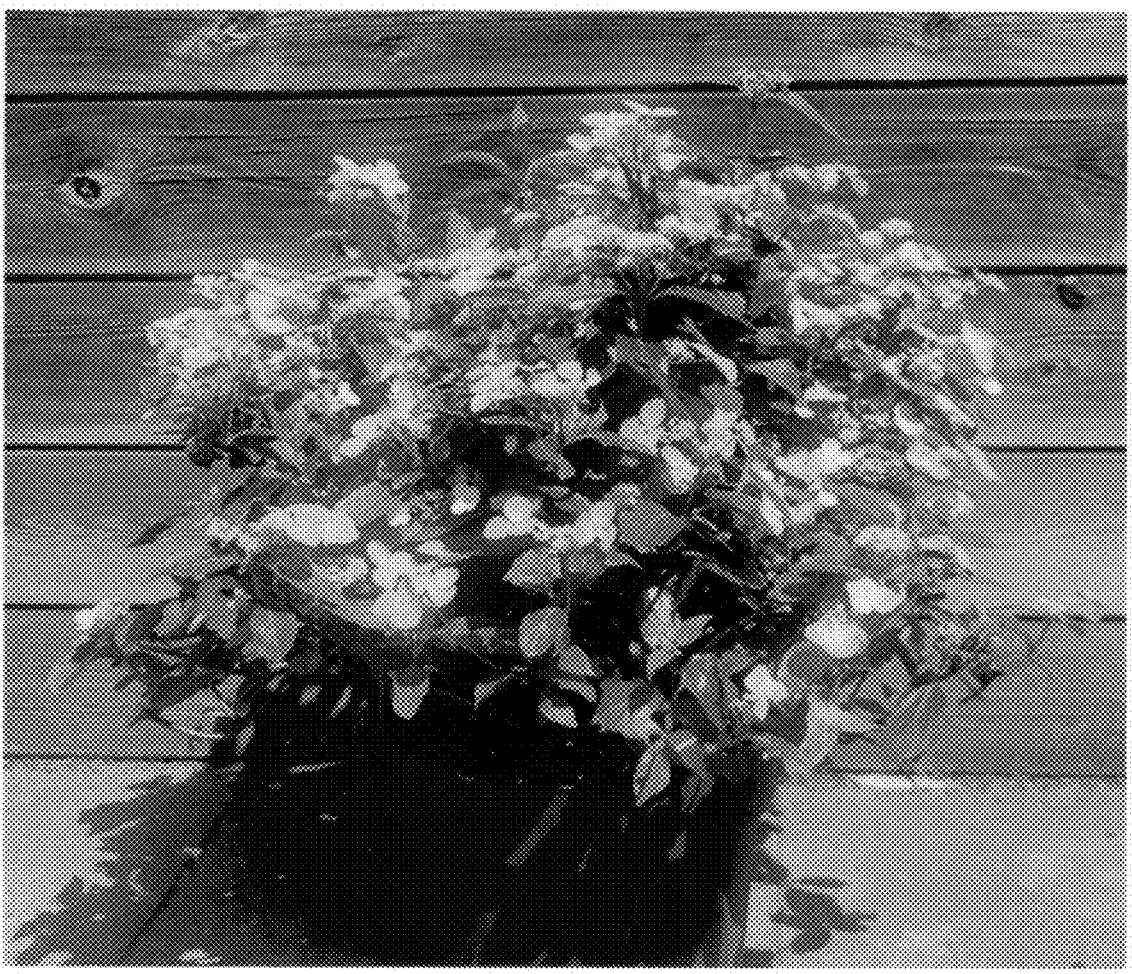

The photograph in FIG. 1 provides a side view of '22B30' in bloom.

Figure 2:
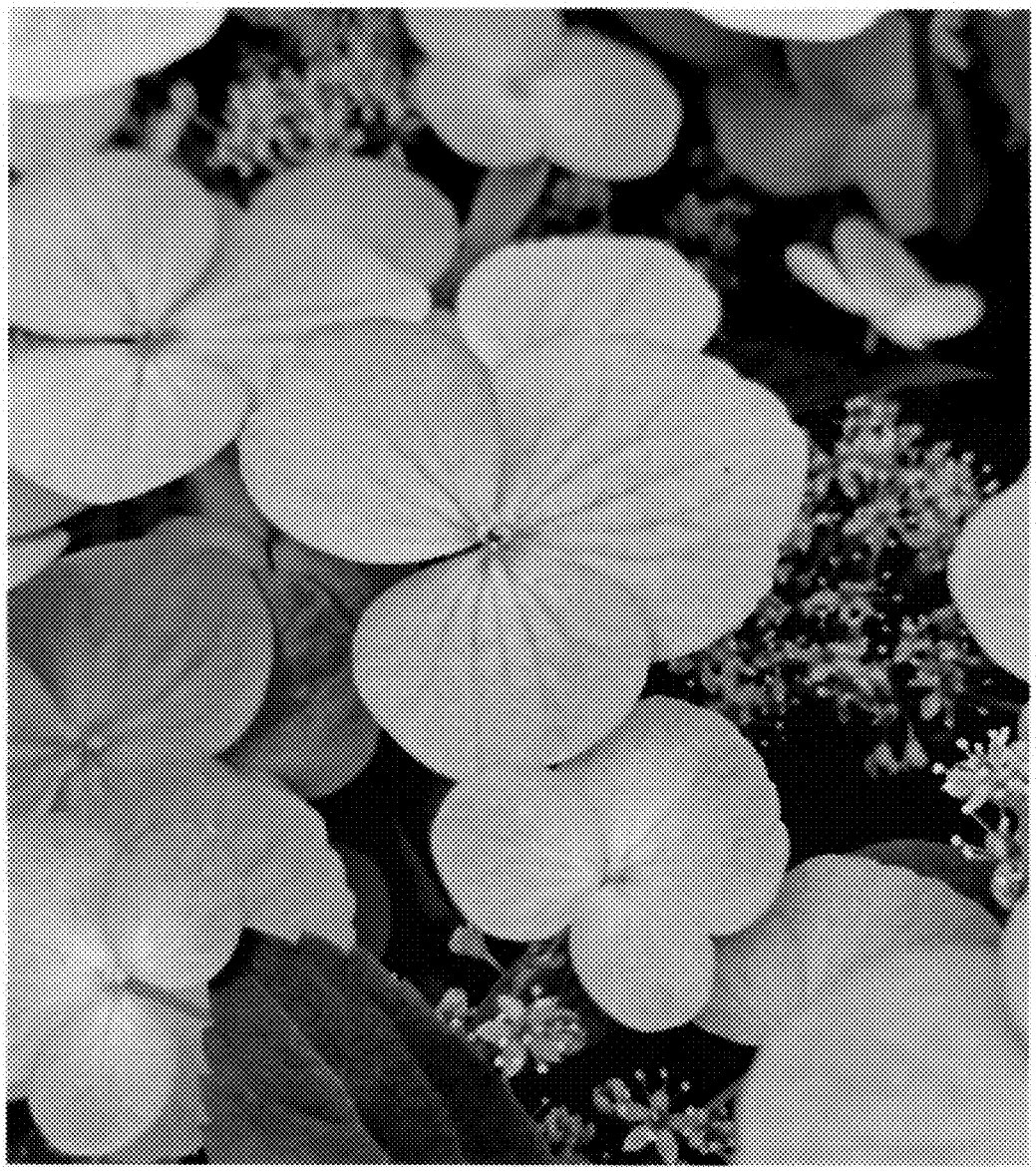

The photograph in FIG. 2 provides a close-up view of the sterile sepals of '22B30'.

Figure 3:
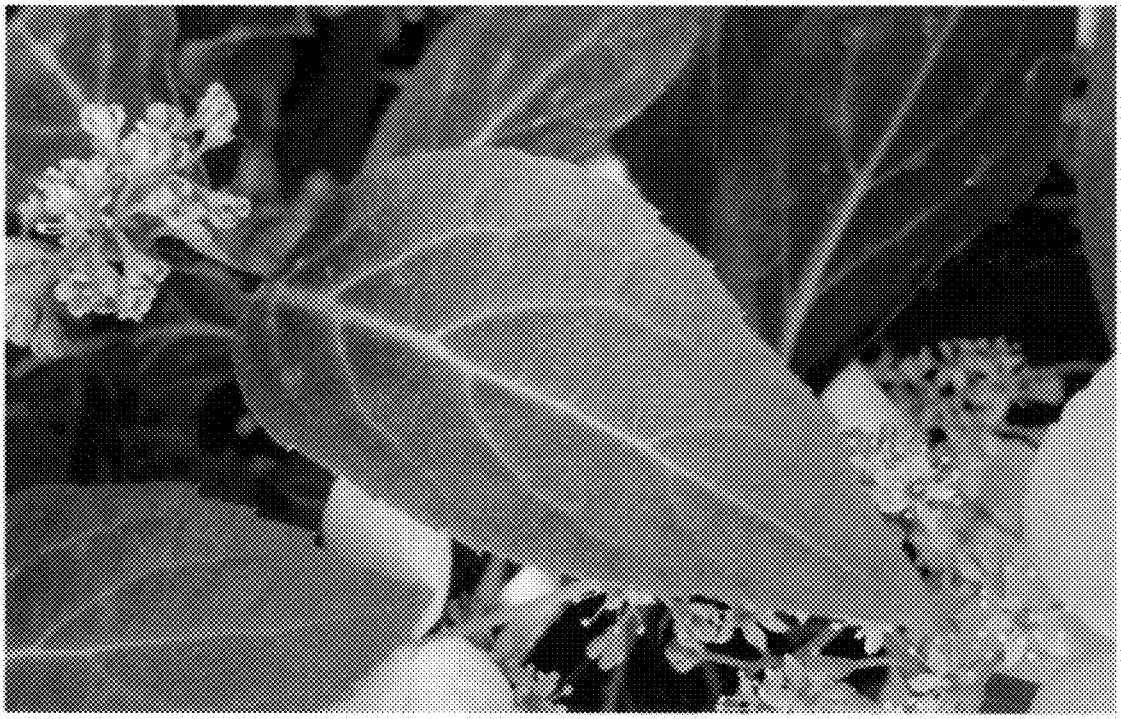

The photograph in FIG. 3 provides a close-up view of a leaf of '22B30'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of 3-year-old plants of '22B30' as grown in 23-cm containers outdoors in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart (2019 reprint) of The Royal Horticultural Society, London, England, except where general color terms of ordinary dictionary significance are used.

General description:

*Blooming period*.—April to June in The Netherlands.

*Plant type*.—Deciduous shrub, lace-cap type *Hydrangea*.

*Plant habit*.—Broadly upright, mounded, and low growing.

*Height and spread*.—An average of 34 cm in height and 60 cm in width as a 3-year-old plant grown in a container, a 5-year-old plant matures in the landscape to 1.5 m in height and width.

*Hardiness*.—At least in U.S.D.A. Zones 6 to 8.

*Diseases and pests*.—No susceptibility and resistance to diseases or pests has been observed.

*Root description*.—Fine, fibrous.

*Propagation*.—Softwood stem cuttings.

*Root development*.—Root initiation; 8 to 10 weeks, time to produce a young plant; 12 months.

*Growth rate and vigor*.—Moderate.

Branch description:

*Branch shape*.—Round.

*Branch strength*.—Strong.

*Branch color*.—Young stems; 144C and 178A, mature stems; 200D, old branches and bark; 200A to 200C.

*Branch size*.—22 cm in length, 8 mm in diameter.

*Branch surface*.—Young; slightly glossy, sparsely to moderately covered with very short adpressed hairs; 0.5 mm in length, too small and sparseness to measure color, mature; matte, older wood; rugose, matte, slightly exfoliating.

*Branch aspect*.—Upright, held in an angle of 65°, varying between 50° and 80° (to vertical).

*Internode length*.—An average of 2.5 cm.

*Branching*.—45 branches from the base.

Foliage description:

*Leaf shape*.—Elliptic to narrowly ovate.

*Leaf arrangement*.—Opposite.

*Leaf division*.—Simple.

*Leaf base*.—Acute.

*Leaf apex*.—Apiculate.

*Leaf margins*.—Serrate.

*Leaf blade lobing*.—Shallow.

*Leaf venation*.—Pinnate, color; upper surface 144C, lower surface 145B.

*Leaf size*.—An average of 4.5 cm in length and 2.2 cm in width.

*Leaf attachment*.—Petiolate.

*Leaf number*.—An average of 10 (5 pairs) per lateral stem.

*Leaf surface*.—Both surfaces smooth and slightly rugose.

*Leaf color*.—Young upper surface; 144A, young lower surface; 144B, margins lightly flushed with 178A, mature upper and lower surface; 145B.

*Petioles*.—4 mm in length and 2 mm in width, color of both surfaces is a blend of 145B and 178B, both surfaces slightly pubescent.

Inflorescence description:

*Inflorescence type*.—Lace-cap type, fertile flowers surrounded by sterile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—4 cm in height, 9 cm in diameter.

*Flower number*.—3 sterile flowers and 80 fertile flowers per panicle.

*Flower fragrance*.—Very light, pleasant fragrance.

*Flower aspect*.—Sterile and fertile flowers; upright to slightly outward.

*Flower size*.—Sterile flowers; 2.7 cm in diameter, 5 mm in depth, fertile flowers; 4 mm in diameter, 3 mm in depth.

*Flower type*.—Rotate.

*Flower buds*.—Sterile flowers: 5 mm in depth, 3 mm in diameter, narrowly cup-shaped, 144A in color, fertile flowers; 2 mm in depth, 1 mm in diameter, obovate in shape, 144C in color.

*Peduncles*.—3 mm in length, 2 mm in width, color; 145B and 178B, surface is matte, slightly pubescent.

*Rachis*.—1 cm in length, 1 mm in width, color; both surfaces145B and 178B, surface is matte, slightly pubescent.

*Pedicels*.—Sterile flowers; 1 cm in length and 1 mm in width, held at an angle of 50° to 60° to horizontal, color; 65C, flushed with 63A to 63B, slightly pubescent surface, fertile flowers; 3 mm in length, 1 mm in width, surface is slightly pubescent with pubescence too small to measure color, held at an angle of 50° to 90° to horizontal, color; 144B to 144C and changing to 65C.

*Petals*.—Sterile flowers; 3, rotate, ovate in shape, broadly acute apex, cuneate base, entire margins, 1.35 cm in length and width, both surfaces are glabrous and matte, color; both surfaces when opening and fully open 62C, fertile flowers; 5, rotate, ovate in shape, broadly acute apex, broadly cuneate base, entire margins, 2 mm in length and 1.5 mm in width, both surfaces are glabrous and matte, color; upper surface when opening and fully open 62C, lower surface when opening and fully open 62D.

*Sepals*.—Sterile flowers; 3 to 4 per flower, rotate, overlapping, broadly ovate in shape, apex is obtuse and occasionally shallowly emarginate, base is broadly cuneate, entire margins with very slight undulation, 1.3 cm in length, 1.2 cm in width, both surfaces glabrous and matte, color: when opening upper surface; 145A to 145B, flushed with 63B, when opening lower surface; 145A to 145B, lightly flushed with 63B at the margins, when fully open upper surface; 63B, N155B in the center, when fully open lower surface; 65A and 65C, lightly flushed with 63B at the margins, fertile flowers; average of 5, acute apex, broadly cuneate base and fused, entire margins, 1 mm in length and width, surfaces are matte and glabrous, color; both surfaces when opening and fully open 62D in color.

Reproductive organs:

*Gynoecium*.—Sterile flowers; 2 pistils, 1 mm in length, stigma; club-shaped, 63C in color, style; 1 mm in length, 64B in color, ovary; minute and not visible, fertile flowers; 2 pistils, 2 mm in length, stigma; club-shaped, 63C in color, style; 1.5 mm in length, 64B in color, ovary; 63C in color.

*Androecium*.—Sterile flowers; 8 stamens, filaments; 2 mm in length, N155B in color, anthers; broadly oblong in shape, 1 mm in length, 4D in color, pollen; none, fertile flowers; 10 stamens, filaments; 2 mm in length, NN155D in color, anthers; broadly oblong in shape, an average of 0.5 mm in length, 9D in color, pollen; none.

*Fruit and seed*.—None observed to date.

It is claimed:

1. A new and distinct cultivar of *Hydrangea* plant named '22B30' substantially as herein illustrated and described.

* * * * *